United States Patent [19]
Lacroix et al.

[11] Patent Number: 4,542,023
[45] Date of Patent: Sep. 17, 1985

[54] FUNGICIDAL SALTS OF ORGANOPHOSPHORUS DERIVATIVES

[75] Inventors: Guy Lacroix, Lyons; Claude Anding, Chaponost; Andrée Viricel, Villeurbanne, all of France

[73] Assignee: Rhone-Poulenc Agrochimie, Lyons, France

[21] Appl. No.: 575,574

[22] Filed: Jan. 31, 1984

[30] Foreign Application Priority Data

Feb. 1, 1983 [FR] France .................... 83 01727
Oct. 13, 1983 [FR] France .................... 83 16499

[51] Int. Cl.$^4$ .................... C07F 9/143; C07F 9/48; A01N 57/00; A61K 31/00
[52] U.S. Cl. .................... 514/126; 260/502.4 R; 260/502.5 E; 260/502.5 R; 260/947; 568/15; 514/114
[58] Field of Search ......... 260/502.4 R, 947, 502.5 E, 260/502.5 R; 568/15; 424/215, 216, 211

[56] References Cited

U.S. PATENT DOCUMENTS

| | | | |
|---|---|---|---|
| 3,507,937 | 4/1970 | Zimmerer | 260/502.4 R |
| 3,637,496 | 1/1972 | Logan et al. | 424/215 |
| 3,702,878 | 11/1972 | Saito | 260/502.4 R |
| 3,711,493 | 1/1973 | George et al. | 260/502.4 R |
| 4,315,765 | 2/1982 | Large | 260/502.5 F |

FOREIGN PATENT DOCUMENTS

| | | | |
|---|---|---|---|
| 1162570 | 2/1984 | Canada | 260/502.4 R |
| 247950 | 12/1969 | U.S.S.R. | 260/502.4 R |

*Primary Examiner*—J. E. Evans
*Attorney, Agent, or Firm*—Burns, Doane, Swecker & Mathis

[57] ABSTRACT

Compounds of the formula:

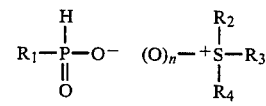

wherein:
 $R_1$=H, OH, alkyl ($C_1$–$C_4$) optionally substituted by halogen, OH or NHOH; optionally substituted phenyl; or alkoxy ($C_1$–$C_4$);
 $R_2$ and $R_3$=alkyl ($C_1$–$C_5$) or optionally substituted phenyl or together=—$(CH_2)_m$—, m=4 or 5;
 $R_4$=alkyl ($C_1$–$C_{18}$), alkenyl ($C_2$–$C_{18}$) or optionally substituted benzyl or phenyl; and
 n=0 or 1. are agriculturally useful as fungicides or bactericides for protecting plants.

13 Claims, No Drawings

FUNGICIDAL SALTS OF ORGANOPHOSPHORUS DERIVATIVES

SUMMARY OF THE INVENTION

The present invention relates generally to novel salts of organophosphorus derivatives, i.e., phosphite or phosphinate derivatives, the preparation of these compounds, fungicidal compositions derived from same and methods of application for the protection of plants employing such derivatives.

Various alkyl phosphite compounds, and, in particular, metal alkyl phosphites have been heretofore proposed as being useful in fungicidal compositions for application to plants. See, for example, British Patent Specification Nos. 1,449,394 and 1,594,635 describing alkyl- and alkali metal or alkaline earth metal-alkyl phosphites as systemic fungicides for the protection of vines against mildew. It has usually been deemed necessary to utilize these metal alkyl phosphites in combination with various contact fungicides, such as maneb, mancozeb, captofol, folpet, etc., to obtain adequate protection.

DESCRIPTION OF THE PREFERRED EMBODIMENTS

It has now been found, surprisingly, that certain novel non-metallic salts of such organo phosphorous derivative fungicides possess valuable prolonged systemic and contact fungistatic and fungicidal activity as well as important bactericidal activity when applied as plant protectants without the need to employ additional fungicidally active compounds.

More particularly applicants have discovered fungicidally active compounds corresponding to the general formula:

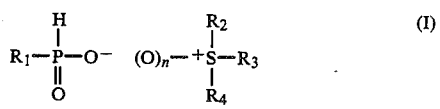

wherein:
- $R_1$ represents a hydrogen atom, a hydroxyl group, a branched or straight chain lower alkyl group containing from 1 to 4 carbon atoms, optionally substituted by hydrogen, hydroxyl or hydroxylamino; phenyl or substituted phenyl; or the group $OR_5$, wherein $R_5$ represents alkyl containing from 1 to 4 carbon atoms;
- $R_2$ and $R_3$, which are identical or different, represent branched or straight chain alkyl containing from 1 to 5 carbon atoms or an optionally substituted phenyl radical, or $R_2$ and $R_3$ together form the group $—(CH_2)_m—$, m being an integer equal to 4 or 5;
- $R_4$ represents a branched or straight chain alkyl group containing from 1 to 18 carbon atoms, which may be optionally substituted by halogen, hydroxyl or hydroxylamino; or alkenyl containing from 2 to 18 carbon atoms or an optionally substituted benzyl or phenyl radical; and
- n is an integer equal to zero or 1.

As used herein, the expression "substituted" benzyl or phenyl encompasses such aromatic rings bearing any of the substituents recited for $R_1$-$R_5$.

Compounds falling within the above formula (I) which are especially preferred by reason of their outstanding fungicidal properties are those wherein $R_1$ is a hydrogen atom, a hydroxyl radical, an alkyl radical having 1 to 4 carbon atoms or an alkoxy radical having 1 to 4 carbon atoms; $R_2$ and $R_3$ are each an alkyl radical having 1 to 4 carbon atoms, in particular methyl and ethyl; and $R_4$ represents methyl or a linear alkyl having 12 to 16 carbon atoms.

The compounds of the general formula I can be prepared by a process, comprising the reaction of a compound of the formula (II):

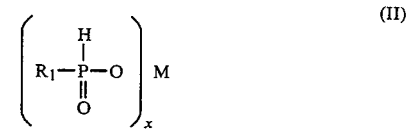

with a sulfonium or sulfoxonium salt of the formula (III), in an aqueous medium, according to the reaction scheme depicted below:

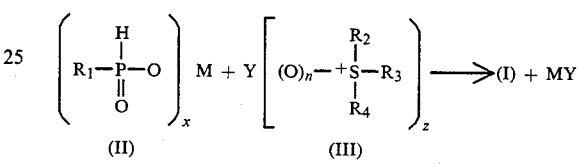

wherein:
- $R_1$, $R_2$, $R_3$, $R_4$ and n have the same meanings as in formula (I) and M is
- either a hydrogen atom, in which case Y is a halogen atom and x and z are equal to 1,
- or an alkaline earth metal atom, in which case Y is the sulfate anion and x and z are equal to 2.

The foregoing process can be carried out according to two variants as follows:

(A) Reacting an acid of the formula (IV)

with a sulfonium or sulfoxonium halide, in an aqueous medium, according to the equation:

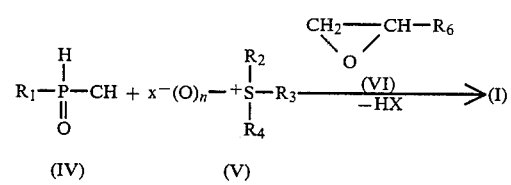

wherein:
- $R_1$, $R_2$, $R_3$, $R_4$ and n have the same meanings as in the formula (I),
- $R_6$ is a hydrogen atom or a methyl radical, and
- x is a halogen atom, i.e., chlorine, bromine, iodine or fluorine, in the presence of a hydracid (e.g., hydrochloric) acceptor, e.g., an alkylene oxide such as ethylene oxide or propylene oxide.

In the case of monosubstituted phosphites (i.e., $R_1=OR_5$), the phosphorous acid ester is prepared in situ by hydrolysis of the corresponding dialkyl phosphite according to the reaction:

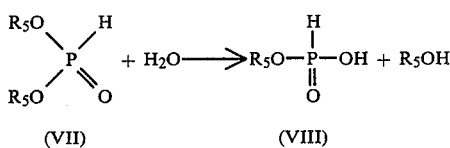

(VII) → (VIII)

(B) Reacting a sulfonium or sulfoxonium sulfate with a substituted phosphite of a metal to provide an insoluble sulfate, in particular, an alkaline earth metal such as calcium or barium, according to the reaction:

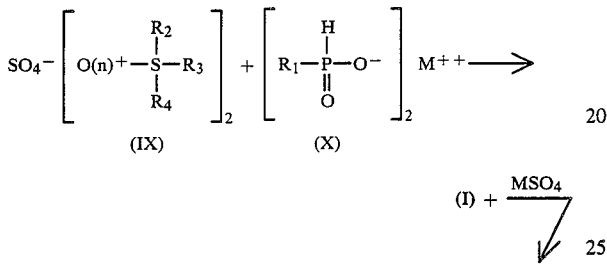

in which $R_1$, $R_2$, $R_3$, $R_4$ and n have the above meanings. The insoluble sulfate precipitates; is filtered off; the filtrate is concentrated and, if necessary, purified.

The following nonlimiting examples illustrate the preparation of the compounds according to the invention as well as the fungicidal properties of certain preferred compounds of formula (I). The structures of the compounds obtained in accordance with the invention were confirmed by nuclear magnetic resonance spectrometry (NMR) (NMR spectra were run on a 60 Megahertz spectrometer).

In the examples illustrating the biological properties of the tested compounds, if plant protection is at least 95%, the product compound is considered to provide complete or total protection against fungal disease; if protection is at least between 80 to 95%, protection is rated as good.

EXAMPLE 1

Sulfoxonium alkylphosphinates and phenylphosphinates

Monoethylphosphinic acid (3.8 g) and trimethylsulfoxonium iodide (8.8 g) are dissolved in water (80 ml). Propylene oxide (20 ml) is added. The medium is then heated for 3 hours at 35° C. The medium is concentrated under reduced pressure (15–20 mm Hg) to give a colorless oil which crystallizes at ambient temperature. The crude product is dissolved in acetonitrile (50 ml) at 40° C. The solution is cooled in a bath of acetone and solid carbon dioxide to obtain product precipitate. The precipitate is filtered off and washed with iced acetonitrile (10 ml) and ether (10 ml). The product is then dried in a vacuum desiccator.

Trimethylsulfoxonium ethylphosphinate (compound No. 1) is obtained as a white hygroscopic solid (4 g) melting at 118° C.

By following the foregoing procedure using phenylphosphinic acid and trimethylsulfoxonium iodide as the starting materials, trimethylsulfoxonium phenylphosphinate (compound no. 11), m.p. 124° C., is obtained.

Following the procedure of Example 1 and using the appropriate phosphonic acid and the appropriate sulfonium iodide as the starting materials, the following compounds are obtained as set forth in Table (I):

TABLE (I)

$$R_1 - \underset{\underset{O}{\|}}{P} - O^- \quad {}^+S \underset{R_3}{\overset{CH_3}{\diagup}} R_4$$

| Compound n° | $R_1$ | $R_3$ | $R_4$ | Physical constants |
|---|---|---|---|---|
| 2 | $C_2H_5$ | $CH_3$ | $CH_3$ | White, very hygroscopic solid |
| 12 | $C_6H_5$ | $CH_3$ | $CH_3$ | M.p. = 135° C. |
| 13 | $C_2H_5$ | $CH_3$ | $C_{12}H_{25}$ | M.p. = 96° C. |
| 14 | $C_6H_5$ | $CH_3$ | $C_{12}H_{25}$ | M.p. = 93° C. |
| 15 | $C_2H_5$ | $CH_3$ | $C_{13}H_{27}$ | M.p. = 90° C. |
| 16 | $C_6H_5$ | $CH_3$ | $C_{13}H_{27}$ | M.p. = 85° C. |
| 17 | $C_2H_5$ | $CH_3$ | $C_{14}H_{29}$ | M.p. = 93–95° C. |
| 18 | $C_6H_5$ | $CH_3$ | $C_{14}H_{29}$ | M.p. = 80–85° C. |
| 19 | $C_2H_5$ | $CH_3$ | $C_{16}H_{33}$ | M.p. = 95–100° C. |
| 20 | $C_6H_5$ | $CH_3$ | $C_{16}H_{33}$ | M.p. = 92–95° C. |
| 33 | $C_2H_5$ | $C_2H_5$ | $C_{12}H_{25}$ | M.P. = 65° C. (vitrification) |
| 34 | H—O—CH(CH_3) | $C_2H_5$ | $C_{12}H_{25}$ | M.p. = 82–85° C. |
| 35 | $C_6H_5$ | $C_2H_5$ | $C_{12}H_{25}$ | Pasty hygroscopic solid |

EXAMPLE 2

Preparation of trimethylsulfonium ethylphosphite (compound no. 3)

Diethyl phosphite (5.5 g) and trimethylsulfonium iodide (8.2 g) are dissolved in water (80 ml). Propylene oxide (20 ml) is added and the mixture is then heated for 6 hours at 35° C. Concentration of the medium under reduced pressure gives a colorless oil (7.9 g) which crystallizes at ambient temperature. The crude product is dissolved in acetonitrile (25 ml) at ambient temperature. The solution is cooled by means of an acetone ice bath. The precipitated product is filtered off and then dried in a vacuum desiccator.

Compound No. 3 is obtained as a very hygroscopic acid (4 g) melting at 58° C.

Following the procedure of Example 2 and using the appropriate reactants as starting materials, the following compounds are prepared:

TABLE II $$R_5 - O - \underset{\underset{O}{\|}}{P} - O^- \quad (O)_n {}^+S \underset{R_3}{\overset{CH_3}{\diagup}} R_4$$

| Compound no. | $R_5$ | n | $R_3$ | $R_4$ | Physical constant |
|---|---|---|---|---|---|
| 4 | H | 0 | $CH_3$ | $CH_3$ | M.p.: 123° C. |
| 5 | H | 1 | $CH_3$ | $CH_3$ | M.p.: 173° C. |
| 6 | $CH_3$ | 0 | $CH_3$ | $CH_3$ | oil $n_D^{20}$: 1.488 |
| 7 | $CH_3$ | 1 | $CH_3$ | $CH_3$ | M.p.: 41° C. |
| 8 | $C_2H_5$ | 1 | $CH_3$ | $CH_3$ | M.p.: 78° C. |
| 21 | H | 0 | $CH_3$ | $C_{12}H_{25}$ | M.p.: 65° C. |
| 22 | $C_2H_5$ | 0 | $CH_3$ | $C_{12}H_{25}$ | M.p.: 80° C. |
| 23 | H | 0 | $CH_3$ | $C_{13}H_{27}$ | M.p.: 65° C. |
| 24 | $C_2H_5$ | 0 | $CH_3$ | $C_{13}H_{27}$ | M.p.: 80° C. |
| 25 | H | 0 | $CH_3$ | $C_{14}H_{29}$ | M.p.: 76° C. |
| 26 | $C_2H_5$ | 0 | $CH_3$ | $C_{14}H_{29}$ | M.p.: 92–93° C. |
| 27 | H | 0 | $CH_3$ | $C_{16}H_{33}$ | M.p.: 80° C. |
| 28 | $C_2H_5$ | 0 | $CH_3$ | $C_{16}H_{33}$ | M.p.: 85° C. |

TABLE II-continued $$R_5-O-\underset{\underset{O}{\|}}{\overset{\overset{H}{|}}{P}}-O^- \quad (O)_n{-}^+\underset{\underset{R_3}{|}}{\overset{\overset{CH_3}{/}}{S}}-R_4$$

| Compound no. | $R_5$ | n | $R_3$ | $R_4$ | Physical constant |
|---|---|---|---|---|---|
| 36 | $C_2H_5$ | 0 | $C_2H_5$ | $C_{12}H_{25}$ | M.p.: 65° C. |

EXAMPLE 3

Preparation of trimethylsulfonium hypophosphite (compound no. 9)

A solution of trimethylsulfonium sulfate (7.5 g) and water (20 ml) is added to a solution of calcium hypophosphite (5.12 g) in water (50 ml), the medium being stirred to precipitate calcium sulfate. Stirring is maintained for 0.5 hour at ambient temperature, after which the precipitate is filtered off. The filtrate is concentrated, the residual oil is taken up in acetonitrile (100 ml) and the insoluble materials are filtered off. The organic solution is concentrated and the resulting oil is triturated in ether (200 ml) to give crystals, which are dispersed in the solvent. The precipitate is filtered off and dried in a vacuum desiccator.

Under these conditions, compound no. 9 is obtained as a white hygroscopic solid (6 g) melting at 115°–118° C.

By following the procedure of Example 3 using calcium hypophosphite or 1-hydroxyethyl-phosphite and the appropriate trialkylsulfonium sulfate as the starting materials, the following compounds are obtained:

TABLE III $$R_1-\underset{\underset{O}{\|}}{\overset{\overset{H}{|}}{P}}-O^- \quad (O)_n{-}^+\underset{\underset{CH_3}{|}}{\overset{\overset{CH_3}{|}}{S}}-R_4$$

| Compound no. | $R_1$ | n | $R_4$ | Physical constant |
|---|---|---|---|---|
| 10 | H | 1 | $CH_3$ | M.p.: 155° C. |
| 29 | H | 0 | $C_{12}H_{25}$ | M.p.: 50° C. |
| 30 | H | 0 | $C_{16}H_{33}$ | M.p.: 80–85° C. |
| 31 | $\underset{HO-CH}{\overset{CH_3}{\|}}$ | 0 | $CH_3$ | M.p.: 90° C. |
| 32 | $\underset{HO-CH}{\overset{CH_3}{\|}}$ | 1 | $CH_3$ | M.p.: 130° C. |

EXAMPLE 4

In vivo test against *Plasmopara viticola*, which is responsible for vine mildew, on vine plants (preventive treatment)

Vine plants (CHARDONNAY variety), cultivated in pots, are treated on both sides of their leaves by spraying with an aqueous emulsion containing the active ingredient to be tested; the emulsion sprayed consists of:
active ingredient to be tested (40 mg)
water (40 cc)
Tween 80 [a surface-active agent consisting of the oleate of an ethylene oxide/sorbitol polycondensate] (0.02 cc).

Emulsifying the composition permits the spraying of an aqueous emulsion containing 1 g/liter of active ingredient to be tested. To obtain emulsion sprays whose concentrations of active ingredient to be tested are less than 1 g/liter, the aqueous emulsion of the composition is suitably diluted with water.

After 48 hours, contamination is effected by spraying the underside of the leaves with an aqueous suspension of fungus spores (about 80,000 units/cc). The pots are then placed for 48 hours in an incubation cell at 100% relative humidity and at 20° C.

The plants are checked 9 days after contamination. Under these conditions, it is found that:
at a dose of 1 g/liter, compounds 3; 25, 31 and 34 provide total protection and compounds 10, 17 and 28 provide good protection;
at a dose of 0.33 g/liter, compounds 1, 19, 21 and 30 provide total protection and compounds 2, 9, 18, 26 and 27 provide good protection.

EXAMPLE 5

In vivo test against *Phytophthora infestans*, which is responsible for tomato mildew 60 to 75 day old tomato plants (MARMANDE variety), cultivated in a greenhouse, are treated by spraying with aqueous emulsions prepared as indicated in Example 3 and containing various concentrations of active ingredients to be tested.

After 48 hours, the treated plants are contaminated with an aqueous suspension of spores (zoosporanges) obtained from a culture of *Phytophthora infestans*, cultivated for 20 days on a medium based on chick-pea flour.

The tomato plants are placed for 48 hours in a chamber at a temperature of 16° to 18° C. and at a relative humidity of 100%. The relative humidity is then brought down to 80%.

The results are observed 8 days after contamination. The results are assessed by evaluating the leaf area invaded by the fungus and are expressed as the "percentage protection", i.e.

$$100\left(1 - \frac{A}{A_c}\right),$$

A being the area invaded by the fungus on the plant in question and $A_c$ being the area invaded by the fungus on the untreated control plant. As in the previous examples, the results are indicated below in the form of "total" or "good" protection.

Under these conditions, it is found that, at a dose of 1 g/liter, compounds 4 and 10 provide total protection.

EXAMPLE 6

In vivo test against *Erysiphe graminis* on barley (barley mildew)

An aqueous emulsion of the active ingredient to be tested is prepared by fine milling of the active compound and has the following composition:

| active ingredient to be tested | 40 mg |
|---|---|
| Tween 80 (a surface-active agent consisting of the oleate of an ethylene oxide/sorbitan polycondensate) | 0.4 ml |
| water | 40 ml |

This aqueous emulsion is then diluted with water to give the desired concentration.

Barley in pots, sown in a mixture of peat and pozzolana, is treated at the 10 cm-high stage by spraying with an aqueous emulsion having the concentration indicated below. The test is repeated twice. After 48 hours, the barley plants are sprinkled with *Erysiphe graminis* spores, the sprinkling being effected using diseased plants.

The results are assessed 10 days after contamination.

Under these conditions, it is found that, at a dose of 1 g/liter, compound 2 provides total protection and compounds 6, 9 and 12 provide good protection.

EXAMPLE 7

In Vitro test against

*Pythium de Baryanum*, which is responsible for damping off,

*Botrytis cinerea*, which is responsible for gray mould.

The compound to be tested is introduced, in the form of an acetone solution (of 1% strength), into a test-tube containing a sterile culture medium above its melting point (70° C.). After mixing, the medium containing the product is run into a Petri dish (10 cm) under aseptic conditions. Series of dishes containing various doses of active ingredient are prepared in this way. After 24 hours, the dishes are inoculated by depositing at the center a mycelium implant (diameter 9 mm) of the fungus studied (Pythium) or a drop of conidia suspension (Botrytis).

A comparison is then made between the rate of growth of the fungus on the medium without the product (control) and on the medium containing the doses described previously; the rate of growth of the fungi is assessed by measuring the diameter of the colony.

Under these conditions, it is found that, at a dose of 0.1 g/liter, compound 4 completely inhibits the growth of the Pythium, whereas compounds 2, 3, 9, 12, 13, 14, 15, 16, 18, 19, 20, 21, 23, 24, 25, 26, 27, 28, 29 and 30 provide good inhibition. Furthermore, at the same dose, compounds 3 and 6 provide good inhibition of *Botrytis cinerea*.

EXAMPLE 8

In vivo test against *Puccinia recondita*, which is responsible for brown rust of cereals.

Wheat plants (TALENT variety) cultivated in a greenhouse, which have reached a height of about 10 cm, are treated by spraying with aqueous emulsions prepared as indicated in Example 3 and containing various concentrations of the compounds according to the invention.

After 48 hours, the treated plants are contaminated with an aqueous suspension of "*Puccinia recondita*" spores, containing about 800,000 spores per ml, prepared from already contaminated plants.

The wheat plants are placed for 48 hours in a chamber at a temperature of about 20° C. and at a relative humidity of 100%. The relative humidity is then brought down to 60%. The condition of the plants is checked on the 15th day after contamination and the percentage protection is determined by the method described in Example 3.

Under these conditions, it is observed that:

at a dose of 1 g/liter, compound nos. 13, 14 and 30 effect total protection and compound nos. 15, 17, 23, 31 and 34 effect good protection, at a dose of 0.3 g/liter, compound nos. 16, 24, 26, 28 and 30 provide good inhibition (protection).

at a dose of 0.1 g/liter, compound nos. 18, 19, 20 and 27 effect total protection.

In vitro tests against bacteria

An agar medium (20 ml) is deposited hot in a series of Petri dishes of diameter 9 mm, and the medium is then left to cool. A 1% strength solution of the substance to be tested, in an organic or aqueous solvent which is inert with respect to the growth of the bacteria under the conditions of the experiment, is simultaneously injected into each Petri dish using a calibrated pipette.

After 24 hours, the contents of the Petri dishes are inoculated with the chosen bacterium and the experiment is then observed in a room at 22° C.±2° C.

The plants are checked 3 days after inoculation by visual comparison of the growth of the bacterial colonies with a control not containing inhibitor (substance to be tested).

Under these conditions, it is observed that:

against *Erwinia amylovora* (INRA:CNBP 1430), compounds:

11, 12, 15, 16, 19, 22, 23, 24 and 27, at a dose of 30 mg/liter, and 13, 14 and 21, at a dose of 10 mg/liter, totally inhibit the growth of the bacterium;

against *Xanthomonas oryzae* (INRA:CNBP 1951), compounds:

27, at a dose of 30 mg/liter, 22, at a dose of 10 mg/liter, 13, 14, 16, 17, 18, 21, 24, 25, 26 and 28, at a dose of 3 mg/liter, and 11, 12, 15, 19 and 23, at a dose of 1 mg/liter, totally inhibit the growth of the bacterium; and against *Corynebacterium michiganense* (INRA:CNBP 2108), compounds:

11, 12, 19 and 27, at a dose of 10 mg/liter, 13, 14, 15, 16, 17, 18, 21, 22, 23, 24 and 26, at a dose of 3 mg/liter, and 25 and 28, at a dose of 1 mg/liter, totally inhibit the growth of the bacterium.

The foregoing examples clearly illustrate the outstanding systemic and contact fungicidal properties of the compositions based on the compounds according to the invention against a variety of families of fungi, in particular the phycomycetes such as *Plasmapora viticola*, the Phytophthora and the Pythium, or the ascomycetes such as Erysiphe sp. (mildews) or botrytis, or the basidiomycetes such as *Puccinia recondita*, or the Fungi Imperfecti such as *Piricularia oryzae*. The excellent bactericidal action of the compounds according to the invention against important agricultural bacteria, such as those of the Erwinia type, those of the Xanthomonas type and other Corynebacterium sp., are also demonstrated.

It is further noted that the compounds of the present invention when applied at fungicidally and bactericidally effective concentrations exhibit selective action and are thus not harmful to treated crops. Accordingly, the active compounds of the invention are advantageously applied at a rate of 0.05 to 5 kg/ha, preferably of 0.1 to 2 kg/ha, although these application rates may vary somewhat depending on plant health, infestation rates, virulence of the fungal or bacterial strain and climate conditions.

For their use in practice, the compounds according to the invention are rarely employed by themselves. Most frequently, they comprise the active ingredients in formulated compositions. These compositions, which can be advantageously applied to plants or the situs thereof to protect same against fungal diseases, contain one or more compounds according to the invention, as the active ingredient, in combination with a solid or liquid agriculturally acceptable carrier optionally including surface-active agents also acceptable for use in agriculture. In particular, conventional inert carriers and surface-active agents can be used in accordance with accepted practices.

Moreover, the compositions of the invention may contain various other ingredients such as, e.g., protective colloids, adhesives, thickeners, thixotropic agents, penetrating agents, stabilizers, sequestering agents and the like, as well as other known active ingredients having pesticidal properties (in particular insecticides or fungicides), properties promoting plant growth (in particular fertilizers) and the like. More generally, the compounds according to the invention can be used in combination with any of the solid or liquid additives corresponding to the usual formulation techniques.

In general, compositions containing 0.5 to 5,000 ppm (parts per million) of active substance are suitable in premixed ready-to-use compositions. The range of 0.5 to 5,000 ppm corresponds to a range of $5 \times 10^{-5}\%$ to 0.5% (percentages by weight).

Relative to compositions suitable for storage and transportation as concentrates suitable for subsequent final mixing, these more advantageously contain from 0.5 to 95% (by weight) of active substance.

Thus, the compositions according to the invention for ultimate agricultural use may contain the active ingredients according to the invention in proportions varying within very wide limits ranging from $5-10^{-5}\%$ to 95% (by weight) depending on the type of formulation desired and storage requirements.

As has already been stated, the compounds according to the invention are generally used in combination with carriers and, if appropriate, surface-active agents.

As used herein, the term "carrier" is defined as an organic or inorganic, natural or synthetic material with which the active ingredient is combined in order to facilitate its application to the plant, to seeds or to the soil. Suitable carrier materials are therefore generally inert and must be agriculturally acceptable and, in particular, not harmful to the plant treated or in any way adversely affect the activity or applicability of the active compounds of the invention. The carrier can be solid (clays, natural or synthetic silicates, silica, resins, waxes, solid fertilizers or the like) or liquid (water, alcohols, ketones, petroleum fractions, aromatic or paraffinic hydrocarbons, chlorohydrocarbons, liquified gases or the like).

The surface-active agents can be an emulsifying, dispersing or wetting agent of ionic or non-ionic type. Preferred examples which may be mentioned are polyacrylic acid salts, lignosulfonic acid salts, phenylsulfonic or naphthalenesulfonic acid salts, polycondensates of ethylene oxide with fatty alcohols, fatty acids or fatty amines, substituted phenols (in particular alkyl phenols or aryl phenols), salts of sulfosuccinic acid esters, taurine derivatives (in particular alkyltaurates) and phosphoric acid esters of polycondensates of ethylene oxide with alcohols or phenols. The presence of at least one surface-active agent is generally essential if the active ingredient and/or the inert carrier are not soluble in water and if the application vehicle is water.

For ultimate agricultural use, the compounds of the formula (I) are therefore generally in the form of compositions and such compositions according to the invention may further vary widely in the form of solid or liquid formulations for specific field or crop applications.

As forms of solid compositions, there may be mentioned dusting powders or sprinkling powders (with an active compound concentration ranging up to 100%) and granules; in particular, those obtained by extrusion, by compaction, by impregnation of a granular carrier or by the formation of granules from a powder (active compound concentration in such granules being between about 1 and 80%).

As forms of liquid compositions or compositions which are to be made up into liquid compositions on application, there may be mentioned solutions, in particular water-soluble concentrates, emulsifiable concentrates, emulsions, suspension concentrates, aerosols, wettable powders (or sprayable powders) and pastes.

The emulsifiable or soluble concentrates most frequently comprise 10 to 80% of active ingredient, and the preformulated emulsions or solutions contain 0.01 to 20% of active ingredient. In addition to the solvent, where necessary, the emulsifiable concentrates can contain 2 to 20% of suitable additives such as stabilizers, surface-active agents, penetrating agents, corrosion inhibitors, dyestuffs and adhesives. The compositions of exemplary concentrates are set forth below:

| active ingredient | 400 g/liter |
| alkali metal dodecylbenzenesulfonate | 24 g/liter |
| 10:1 ethylene oxide/nonylphenol condensate | 16 g/liter |
| cyclohexanone | 200 g/liter |
| aromatic solvent q.s. | 1 liter |

Another typical formulation of an emulsifiable concentrate employs the following constituents:

| active ingredient | 250 g |
| epoxidized vegetable oil | 25 g |
| mixture of an alkylarylsulfonate and a polyglycol ether of fatty alcohols | 100 g |
| dimethylformamide | 50 g |
| xylene | 575 g |

Using the foregoing concentrates, emulsions of any desired concentration, which are particularly suitable for application to the leaves, can be obtained by dilution with water.

Suspension concentrates in accordance with the present invention which can also be applied by spraying, are prepared so as to give a stable fluid product which does not form a deposit, and such suspensions usually contain from 10 to 75% of active ingredients, from 0.5 to 15% of surface-active agents, from 0.1 to 10% of thixotropic agents, from 0 to 10% of suitable additives such as antifoam agents, corrosion inhibitors, stabilizers, penetrating agents and adhesives, and, as the carrier, water or an organic liquid in which the active ingredient is sparingly soluble or insoluble; certain organic solids, or inorganic salts, can also be dissolved in the carrier to assist in preventing sedimentation or to prevent solvent freezing.

The wettable powders (or sprayable powders) are usually prepared so as to contain 20 to 95% of active ingredient, and usually contain, in addition to the solid carrier, from 0 to 5% of a wetting agent, from 3 to 10% of a dispersing agent and, where necessary, from 0 to 10% of one or more stabilizers and/or other additives such as penetrating agents, adhesives, anti-caking agents, dyestuffs and the like.

Various exemplary compositions of wettable powders are given below:

| active ingredient | 50% |
|---|---|
| calcium lignosulfonate (deflocculant) | 5% |
| isopropylnaphthalenesulfonate (anionic wetting agent) | 1% |
| anti-caking silica | 5% |
| kaolin (filler) | 39% |

A 70% strength [i.e. concentration of active component] wettable powder:

| active ingredient | 700 g |
|---|---|
| sodium dibutylnaphthylsulfonate | 50 g |
| 3:2:1 naphthalenesulfonic acid/phenylsulfonic acid/formaldehyde condensate | 30 g |
| Kaolin | 100 g |
| Champagne chalk | 120 g |

A 40% strength wettable powder:

| active ingredient | 400 g |
|---|---|
| sodium lignosulfonate | 50 g |
| sodium dibutylnaphthalenesulfonate | 10 g |
| silica | 540 g |

A 25% strength wettable powder:

| active ingredient | 250 g |
|---|---|
| calcium lignosulfonate | 45 g |
| mixture of equal parts by weight of Champagne chalk and hydroxyethylcellulose | 19 g |
| sodium dibutylnaphthalenesulfonate | 15 g |
| silica | 195 g |
| Champagne chalk | 195 g |
| kaolin | 281 g |

A 25% strength wettable powder:

| active ingredient | 250 g |
|---|---|
| isooctylphenoxy-polyoxyethylene-ethanol | 25 g |
| mixtures of equal parts by weight of Champagne chalk and hydroxy-ethylcellulose | 17 g |
| sodium aluminosilicate | 543 g |
| kieselguhr | 165 g |

A 10% strength wettable powder:

| active ingredient | 100 g |
|---|---|
| mixture of sodium salts of saturated fatty acid sulfates | 30 g |
| naphthalenesulfonic acid/formaldehyde condensate | 50 g |
| kaolin | 820 g |

Water-soluble powders are usually obtained by mixing water from 20 to 95% by weight of the active ingredient with from 0 to 10% of an anti-caking filler, the remainder consisting of a water-soluble solid carrier, in particular a salt.

The composition of a typical soluble powder is given below:

| active ingredient (compound no. 2) | 70% |
|---|---|
| anionic wetting agent | 0.5% |
| anti-caking silica | 5% |
| sodium sulfate (solid carrier) | 24.5% |

To obtain these wettable or soluble powders, the active ingredients are intimately mixed with the additional substances in suitable mixers, and the mixture is ground in mills or other suitable grinders. This gives powders of advantageous wettability and suspendability; they can be suspended or dissolved in water at any desired concentration, and the resultant suspension can be used very advantageously, in particular, for application to the leaves of the plants to be protected.

As indicated above, aqueous dispersions and aqueous emulsions, e.g. compositions obtained by diluting a wettable powder or an emulsifiable concentrate according to the invention with water, are included within the general scope of the present invention. The emulsions can be of the water-in-oil or oil-in-water type and may have a thick consistency similar to that of "mayonnaise".

Granules, which are intended to be placed on the soil, are usually prepared so as to have dimensions of between 0.1 and 2 mm, and can be manufactured by agglomeration or impregnation. In general, such granules contain 0.5 to 25% of active ingredient and 0 to 10% of additives such as stabilizers, slow release modifiers, binders and solvents.

An example of a granular composition is as follows:

| active ingredient | 50 g |
|---|---|
| epichlorohydrin | 2.5 g |
| cetyl polyglycol ether | 2.5 g |
| polyethylene glycol | 35 g |
| kaolin (particle size: 0.3 to 0.8 mm) | 910 g |

In the above instance, the active ingredient is mixed with the epichlorohydrin and the mixture is dissolved with 60 g of acetone; the polyethylene glycol and the cetyl polyglycol ether are then added. The kaolin is moistened with the solution obtained and the acetone is then evaporated off in vacuo. Microgranules of this type are advantageously used for combating fungi in the soil.

The compounds of the formula (I) can also be used in the form of dusting powders; it is also possible to use a composition comprising active ingredient (50 g) and talc (950 g); it is further possible to use a composition comprising active ingredient (20 g), finely divided silica (10 g) and talc (970 g), these constituents being mixed and ground and the mixture applied by dusting.

While the invention has been described and illustrated with reference to certain preferred embodiments thereof, those skilled in the art will appreciate that various changes, modifications and substitutions can be made therein without departing from the spirit of the invention. For example, application rates other than those preferred ranges set forth hereinabove may be applicable due to variations in soils and planting characteristics, etc. Moreover, the specific results observed with respect to fungal and bacterial control as well as crop selectivity may vary depending on the specific active compounds selected and whether same are used alone or in combination with each other, i.e., mixture, or with other known agents. Also, the specific formulation and the manner of applying same, e.g., soil drench, foliar spray, etc., may affect results. Accordingly, such expected changes and variations in results are contemplated in accordance with the objects and practices of the present invention. It is intended, therefore, that the invention be limited only by the scope of the claims which follow.

We claim:

1. An organophosphorus derivative, of the formula (I)

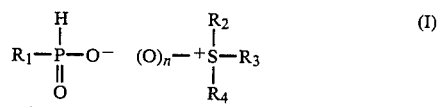

wherein:

$R_1$ represents hydrogen, hydroxyl, lower alkyl group of from 1 to 4 carbon atoms optionally substituted by halogen, hydroxyl or hydroxylamino; an optionally substituted phenyl group; or the group $OR_5$ wherein $R_5$ represents a lower alkyl group of from 1 to 4 carbon atoms;

$R_2$ and $R_3$, which are identical or different, represent an alkyl group of from 1 to 5 carbon atoms or an optionally substituted phenyl group; or $R_2$ and $R_3$ together form a $-(CH_2)-_m$ group, m being an integer equal to 4 or 5;

$R_4$ represents a straight or branched chain alkyl group of from 1 to 18 carbon atoms optionally substituted by halogen, hydroxyl or hydroxylamino; an alkenyl group of from 2 to 18 carbon atoms; or an optionally substituted benzyl or phenyl radical; and n is an integer equal to zero or 1.

2. A derivative according to claim 1, wherein $R_1$ is a hydrogen atom, hydroxyl, an alkyl group having 1 to 4 carbon atoms, an alkoxy radical having 1 to 4 carbon atoms or a phenyl group; $R_2$ and $R_3$ are each an alkyl group having 1 to 4 carbon atoms and $R_4$ is methyl or a linear alkyl group having 12 to 16 carbon atoms.

3. A derivative according to claim 1, wherein $R_1$ is hydroxyl, an alkyl group having 1 to 4 carbon atoms or an alkoxy group having 1 to 4 carbon atoms, and $R_2$, $R_3$ and $R_4$ are each a methyl group.

4. A derivative according to claim 1, wherein $R_1$ is ethyl.

5. A fungicidal and/or bactericidal composition for protecting plants comprising an active compound according to claim 1 in combination with an agriculturally acceptable carrier.

6. A composition according to claim 5, wherein said active compound is present in said composition in an amount ranging between about 0.5 to 5000 ppm.

7. A composition according to claim 5, wherein said active compound is present in said composition in an amount ranging between about 0.5 to 95% by weight.

8. A composition according to claim 5, further comprising a surface-active agent.

9. A composition according to claim 5, wherein said composition is in formulated form suitable for application to plants or the situs thereof, said formulated form comprising wettable powders, sprayable powders, dusting powders, granules, acqueous or organic emulsifiable concentrates, emulsions, suspensions or aerosols.

10. A method for protecting plants against diseases, comprising applying thereto or to the situs thereof a derivative according to any of claims 1 to 4.

11. A method for protecting plants against diseases comprising applying thereto or to the situs thereof a composition according to claim 5.

12. A method according to claim 11, wherein said composition is applied at a rate equal to 0.05 to 5 kg/ha.

13. A method according to claim 12, wherein said rate is 0.1 to 2 kg/ha.

* * * * *

UNITED STATES PATENT AND TRADEMARK OFFICE
CERTIFICATE OF CORRECTION

PATENT NO. : 4,542,023
DATED : September 17, 1985
INVENTOR(S) : Guy LACROIX et al It is certified that error appears in the above-identified patent and that said Letters Patent is hereby corrected as shown below:

Column 2, lines 50-55 should read:

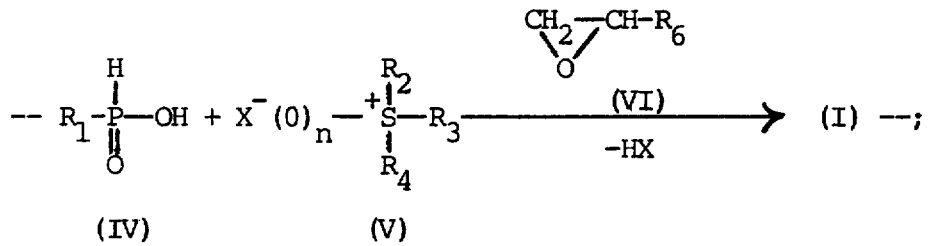

Column 3, line 11, after "phosphate", kindly insert --or phosphinate--.

Column 5, line 32, delete "1-hydroxyethyl-phosphite" and kindly insert -- 1-hydroxyethylphosphinate --.

Signed and Sealed this

Second Day of September 1986

[SEAL]

Attest:

*Attesting Officer*

DONALD J. QUIGG
*Commissioner of Patents and Trademarks*